(12) United States Patent
Moore et al.

(10) Patent No.: US 11,373,551 B2
(45) Date of Patent: Jun. 28, 2022

(54) LOW COST HAPTIC FORCE MEDICAL INSTRUMENT INSERTION SIMULATOR

(71) Applicant: The Penn State Research Foundation, University Park, PA (US)

(72) Inventors: Jason Z. Moore, State College, PA (US); Scarlett Miller, State College, PA (US); Sven Gunnar Bilen, State College, PA (US); Joseph Portelli, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 17/054,307

(22) PCT Filed: May 10, 2019

(86) PCT No.: PCT/US2019/031678
§ 371 (c)(1),
(2) Date: Nov. 10, 2020

(87) PCT Pub. No.: WO2019/217789
PCT Pub. Date: Nov. 14, 2019

(65) Prior Publication Data
US 2021/0097890 A1 Apr. 1, 2021

Related U.S. Application Data

(60) Provisional application No. 62/670,237, filed on May 11, 2018.

(51) Int. Cl.
*G09B 23/28* (2006.01)
*A61B 34/10* (2016.01)
(Continued)

(52) U.S. Cl.
CPC ............ *G09B 23/285* (2013.01); *A61B 34/10* (2016.02); *A61B 34/30* (2016.02); *G09B 9/00* (2013.01); *G09B 23/30* (2013.01)

(58) Field of Classification Search
CPC ...... G09B 23/28; G09B 23/285; G09B 23/30; G09B 9/00; A61B 34/10; A61B 34/30
See application file for complete search history.

(56) References Cited

U.S. PATENT DOCUMENTS

| 3,795,061 A | 3/1974 | Sarnoff et al. |
|---|---|---|
| 5,037,306 A | 8/1991 | van Schoonhoven |

(Continued)

FOREIGN PATENT DOCUMENTS

| CN | 105009185 A | 10/2015 |
|---|---|---|
| CN | 105448172 A | 3/2016 |

(Continued)

OTHER PUBLICATIONS

International Search Report dated Jul. 22, 2019; International Application No. PCT/US2019/031678.

*Primary Examiner* — Timothy A Musselman
(74) *Attorney, Agent, or Firm* — Dinsmore & Shohl LLP

(57) ABSTRACT

A haptic needle insertion simulator includes a syringe compartment having a cavity and a retractable needle at an end of the syringe compartment. The needle is operable to retract into the syringe compartment when pushed against a surface. The cavity is configured to provide a force profile felt by a user holding the simulator and simulating a realistic feeling of insertion force.

14 Claims, 4 Drawing Sheets

(51) Int. Cl.
  *A61B 34/30*  (2016.01)
  *G09B 9/00*  (2006.01)
  *G09B 23/30*  (2006.01)

(56) References Cited

U.S. PATENT DOCUMENTS

| | | |
|---|---|---|
| 8,408,918 B2 | 4/2013 | Hu et al. |
| 8,714,984 B2 | 5/2014 | Mach |
| 9,443,445 B2 | 9/2016 | Laurusonis et al. |
| 9,489,868 B2 | 11/2016 | Smith et al. |
| 2012/0219937 A1 | 8/2012 | Hughes et al. |
| 2013/0296736 A1 | 11/2013 | Svennson |
| 2014/0011169 A1 | 1/2014 | Mourton |
| 2014/0276413 A1 | 9/2014 | Baker et al. |
| 2014/0276568 A1 | 9/2014 | Worden et al. |
| 2014/0364812 A1 | 12/2014 | Lumme et al. |
| 2015/0235571 A1 | 8/2015 | Alexandersson |
| 2016/0049098 A1 | 2/2016 | Swanson et al. |
| 2016/0155363 A1 | 6/2016 | Rios et al. |
| 2018/0005547 A1* | 1/2018 | Baker .................... G09B 23/30 |
| 2018/0225992 A1* | 8/2018 | Gonsalves ............... G09B 5/02 |

FOREIGN PATENT DOCUMENTS

| | | |
|---|---|---|
| DE | 102005062610 A1 | 6/2007 |
| DE | 102005062611 A1 | 6/2007 |
| GB | 2519637 A | 4/2015 |
| WO | 33054834 A1 | 7/2003 |
| WO | 2011151315 A1 | 12/2011 |
| WO | 2016026821 A1 | 2/2016 |
| WO | 2016028821 A1 | 2/2016 |
| WO | 2016078870 A1 | 5/2016 |
| WO | 2018035310 A1 | 2/2018 |

\* cited by examiner

LOW COST HAPTIC FORCE MEDICAL INSTRUMENT INSERTION SIMULATOR

CROSS REFERENCE TO RELATED APPLICATIONS

This application is the U.S. National Stage of PCT/US2019/031678 filed May 10, 2019, which claims priority to U.S. Provisional Patent Application Ser. No. 62/670,237, filed May 11, 2018, the entire content of both are incorporated herein by reference in their entirety.

GOVERNMENT SUPPORT

This invention was made with government support under Grant No. HL127316, awarded by the National Institutes of Health. The Government has certain rights in the invention.

BACKGROUND OF THE INVENTION

The force created during actual insertion of a medical instrument such as a needle into tissue is very complex such as shown in FIG. 2. Traditionally these complex prescribed force profiles could only be simulated through motor drivers in expensive robotic systems such as the current state of the art robotic Central Venous Catheterization system, which utilizes an approximately $10,000 robot to provide realistic force feedback, with a retractable needle syringe. In this system, the robot provides the active force feedback while the retractable syringe simply retracts with minimal force.

SUMMARY OF THE INVENTION

The low cost haptic force medical instrument insertion simulator of the present invention would allow for low cost simulation of the visual illusion and haptic force resistance of inserting a medical instrument. The medical instrument may include, but not limited to, syringes, winged epidural needles, brachytherapy needles, biopsy devices, scalpels, medical probes and other cutting instruments.

Such a system could be a valuable trainer to help train new medical residents in performing numerous types of needle insertion procedures including, but not limited to, placing nerve blocks, brachytherapy (needle based radiation cancer treatment), biopsy, and venous catheterization procedures. Insertion simulators for other medical devices, such as knives and probes would also be useful.

The haptic needle insertion simulator may include an instrument body and a retractable needle, knife or probe at an end of the instrument body. The needle, knife or probe may be operable to retract into the instrument body when pushed against a surface.

In one embodiment, the haptic medical instrument insertion simulator may include an internal variable dampener for generating the haptic force resistance. The internal variable dampener includes a cavity having a variable profile and being filled with a fluid within the instrument body.

The haptic medical instrument insertion simulator may further include a locking mechanism for locking the cartridge in a use position in the instrument body. The locking mechanism may include compliance of the cartridge with the instrument body, a mechanical release or by removing the needle, knife or probe.

The haptic medical instrument insertion simulator may include a cartridge disposed within the instrument body. The cartridge may be filled with synthetic material that the back of the needle, knife or probe penetrates into and the material penetration creates the haptic force that is felt by the user advancing the instrument.

In an example, the haptic simulator is a haptic needle insertion simulator in accordance with an embodiment of the present invention. The haptic needle insertion simulator may include a syringe body and a retractable needle at an end of the syringe compartment. The needle may be operable to retract into the syringe body when pushed against a surface. The syringe body may include a cavity configured to provide a force profile felt by a user holding the simulator and simulating a realistic feeling of insertion force.

The haptic needle insertion simulator may further include a cartridge disposed in the cavity, wherein the cartridge is filled with synthetic material that the back of the needle penetrates into and the material penetration creates the haptic force that is felt by the user advancing the syringe.

In one embodiment, the cartridge is rotatable for repeated use. The cartridge may also be detachable or disposable.

In one embodiment, the haptic needle insertion simulator may include more than one cartridge, each providing a different haptic force. This single cartridge may provide a unique level of force for each unique cartridge. Or the cartridge may provide varying levels of force based on rotational or translational position.

In one embodiment, the cartridge may contain one or more layers that provide fluctuations in force upon insertion of the needle.

The device and method of the present invention can be applied to any hand held haptic skill learning device, including but not limited to, needles, trocars, catheters, bone cutting and drilling devices, etc. The difference in the devices would be that the handle and what is attached to the handle would be made to mimic what is used in practice. For example, a syringe would include a syringe body and a needle. A knife would include a knife handle and a razor blade. A drilling device would include a handle and a drill bit. A catheter would include a handle and a catheter tube.

BRIEF DESCRIPTION OF THE INVENTION

DETAILED DESCRIPTION OF THE INVENTION

Overview

The present invention is directed to a low cost haptic retractable medical instrument insertion simulator. The device allows for a medical instrument to retract into the instrument body when pushed on a phantom surface and to generate a haptic resistance force feedback to a user handling the medical instrument. The present device can be made to replicate or mimic any medical instrument, including but not limited to syringes, winged epidural needles, brachytherapy needles, biopsy devices, scalpels, medical probes and other cutting instruments.

Figure 1A:
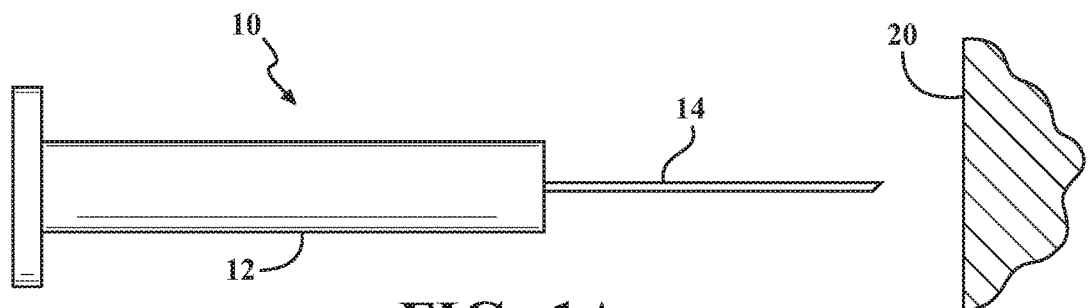
FIGS. 1A-1C are cross-sectional views showing a haptic needle insertion simulator in accordance with an embodiment of the present invention providing a simulation of a needle inserting into a phantom surface and giving a realistic feeling of insertion force.
Figure 1B:
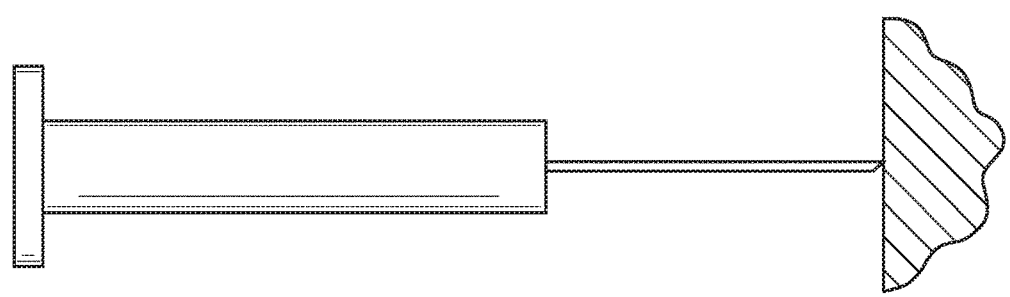
Figure 1C:
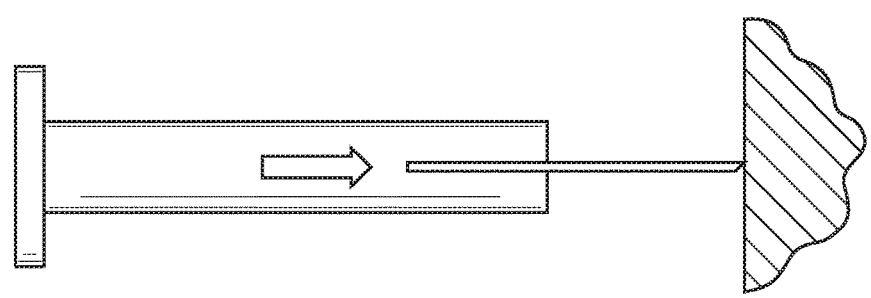
Figure 2:
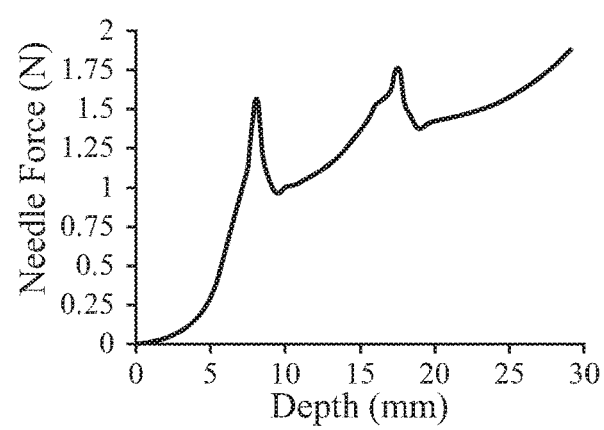
FIG. 2 is a graph showing a force profile for a typical central venous catheterization needle insertion.

In the case of syringes or needles, the needle insertion process involves pushing a needle into tissue while pulling the plunger back at the same time, therefore the force created during actual needle insertion into tissue has a very complex force profile, such as what is shown in FIG. 2. FIGS. 1A-1C illustrate an example of a haptic force needle insertion simulator device 10, which replicates or simulates the forces felt by a user operating a retractable syringe. The haptic force needle insertion simulator device 10 includes a syringe body 12 and a needle 14 which can retract into the syringe body 12. FIG. 1B shows when the needle makes contact with a surface 20. When the haptic force needle insertion simulator device 10 is pushed such that the needle 14 is pushed against the phantom surface 20, the retractable needle 14 attached at one end of the syringe body 12 retracts into the syringe body 12 to provide a visual illusion that the needle is penetrating the phantom material, as shown in FIG. 1C. Internally prescribed force is applied to simulate a realistic insertion force and is felt by the user holding the simulator. By applying this force internally, the need for the expensive robot is eliminated. This device allows for free 360° movement of the person's hand.

The present device may use a variety of methods to simulate the actively prescribed force during the needle retraction, including but not limited to electrical methods, mechanical methods such as material fracture, material compliance or springs, magnets, pneumatic methods, hydraulic methods such as electrorheological fluids, alone or in combination. Although these methods are described as follows using the needle retraction as an example, the methods can also be used to simulate the haptic force encountered in other types of medical instruments.

Methods to Create Internal Force

There are numerous ways for the retractable needle system to create a prescribed force without the use of a robot. These force creation methods include but not limited to any of the following or any combination of the following:

Electrical
    Lead screw motor
    Linear motor
    Electromagnetic
    Magnets Mechanical
    Mechanically positioned deflection elements
    Friction, linear and/or rotary
    Material fracture Pneumatic and Hydraulic
    Variable leaking dampener
    Electrorheological fluid
    Pressure and flow control, internal or external
    Pump, internal or external Electrical Creation of Force Force can be internally created by electrically powered devices. This would include rotary electric motors being utilized to apply force to a lead screw that would in turn apply force to the retractable needle. This would also include the use of a linear motor system to apply force to the retractable needle. This would also include more simple electromagnets that could be electrically controlled to apply either constant force or variable force based on prescribed inputs.

Use of Magnets to Create Force

Magnets could be utilized to prescribe force to the retractable needle. These magnets could either repel or retract each other or magnetic material at specific retractable needle positions. The magnet's position could be fixed or could be variable to allow for varying levels of force to be applied.

Pneumatic and Hydraulic Methods to Create Force

Pneumatics and/or hydraulics could be utilized to create the desired force, where the movement of fluid is either powered or controlled to produce the desired force.

Figure 3A:
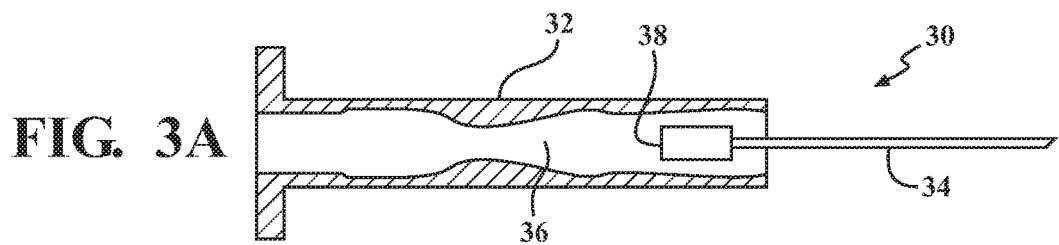
FIGS. 3A-3B are cross-sectional views showing a haptic needle insertion simulator with an internal variable leaking dampener in accordance with an embodiment of the present invention.
Figure 3B:
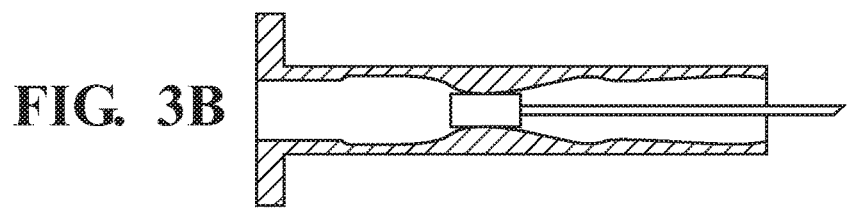

A dampener could be utilized to create a desired force. As illustrated in FIGS. 3A-3B, a variable leaking dampener 30 could be used to create force that varies according to the position of the retracted needle. A fluid dampener is placed inside the haptic force needle insertion simulator device. The dampener features a cavity 36 with a variable internal profile and filled with liquid, encased in the syringe body 32. The dampener also includes a resistance piece 32 attached to the back of the needle 34. This dampener varies the leaking area based on how deep the needle is. As shown in FIG. 3A, as the back of the needle travels to a wider location, the dampener provides little resistance and allows a large volume flow rate of liquid around the dampener. In FIG. 3B, as the dampener at the back of the needle travels to a narrower location, the dampener provides higher resistance and allows a low volume flow rate of liquid around the needle. The system could also be made such that the profile could be easily changed by replacing one part, or rotating or sliding a component on the outside and therefore allow for different profiles to be easily mechanically set into the device. This system also has the added benefit that increased speed will easily translate to increased force, just as in actual tissue insertion.

Inside the dampener, electrorheological fluid could be utilized to allow for quickly varying the viscosity of the fluid and therefore allow for quickly changing of the force profile. This type of fluid changes its viscosity when electrical currents are applied.

Valves could be utilized to actively control the fluid pressure and/or flow either internally in the incased device or externally through attached hoses. Also pumps or accumulated pressure sources could be utilized to actively control the fluid pressure and/or flow either internally in the encased device or externally through attached hoses.

Mechanical Creation of Force

Mechanical means of creating constant or variable force could be applied to the retractable needle. This could include flexible spring type materials, which would vary force based on position. This could also include linear or rotary friction. For example, by applying different coefficients of friction to the retractable needle, the friction force could vary while the retractable needle is inserted. This could also include the physical fracturing of material to allow for the buildup and release of force. As an example, the force could build up and then cause an internal element to break which would quickly drop the force level.

Figure 4A:
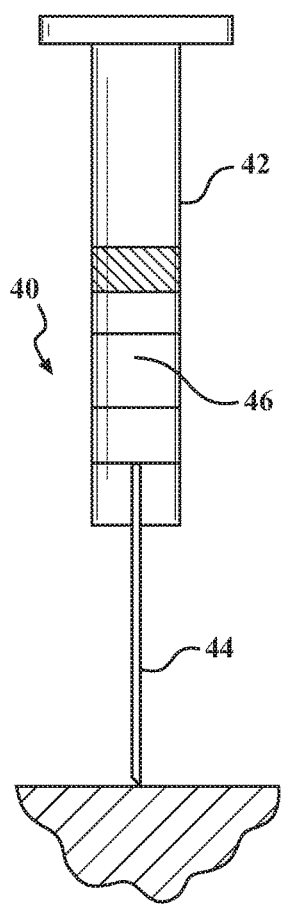
FIGS. 4A-4C are cross-sectional views showing mechanical fracture of materials used in a haptic needle insertion simulator to produce realistic forces.
Figure 4B:
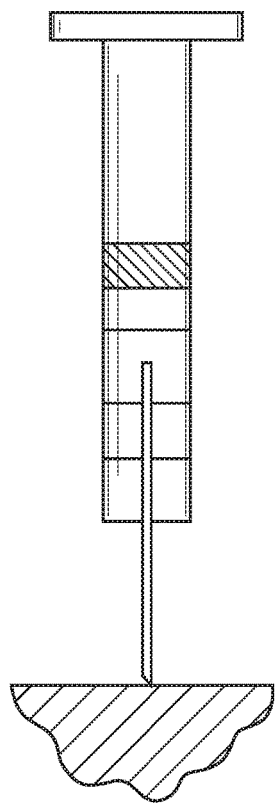
Figure 4C:
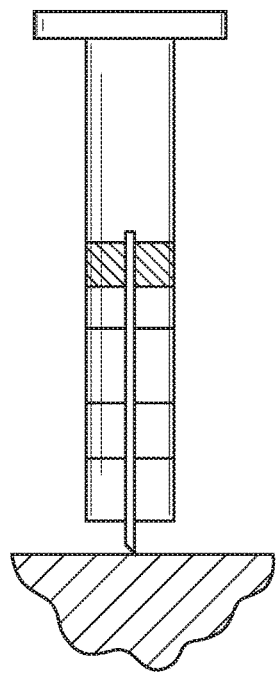

In an exemplary needle retraction simulator 40 illustrated in FIGS. 4A-4C, a material 46 would physically fracture inside the syringe body 42 to create a realistic force feedback feel. A variety of different materials and material thicknesses inside the syringe body 42 allow for a complex force to be felt by the user upon simulated insertion via needle retraction when the back of the retractable needle 44 breaks through different materials. These fracture elements may be replaced into the syringe via a replaceable cartridge system. If a replaceable cartridge is used, this cartridge containing the fracture elements would be replaced after one or more needle insertions. Different combinations of materials and material thicknesses would produce different force profiles. This system of material fracture force creation could be used by itself or could be combined with the other force creating options mentioned herein.

Detachable Cartridges

Figure 5:
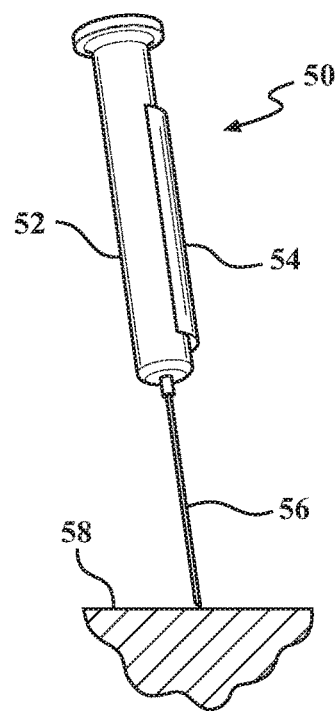
FIG. 5 is a perspective view of a haptic needle insertion simulator with a cartridge in accordance with an embodiment of the present invention.

FIG. 5 illustrates an example of a low cost needle insertion simulator 50 having a detachable cartridge 54. As shown in FIG. 5, the syringe 50 contains a detachable cartridge 54 embedded or inserted in the syringe body 52 and a retractable needle 56. When the needle is pushed on the testing surface 58, the needle retracts into the cartridge, while visually appearing as penetrating into the testing surface. The cartridge may be filled with synthetic material that the back of the needle penetrates into. This material penetration creates the haptic force that is felt by the users advancing the syringe. The cartridge can be rotated to allow for additional penetrations, either continuously or between indexed positions. After the cartridge has been used, it may be discarded and a new cartridge can be put into the syringe. Different cartridges may create different force profiles to provide the user with a diverse patient anatomy training experience. Alternatively, different rotary positions may provide different profiles. The cartridge may be made in a number of ways using a variety of materials. Possible materials may include but not limited to thin plastics of: PTFE, PVC, Polycarbonate, ABS and UHMW Any kind of material may be used if offering the steep rises and falls of insertion force that is desired for training.

Figure 6A:
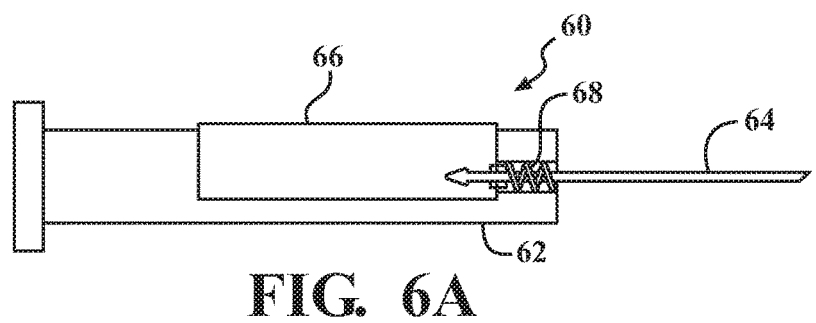
FIGS. 6A-6C are cross-sectional views showing a haptic needle insertion simulator with a detachable cartridge and locking mechanisms in accordance with an embodiment of the present invention.
Figure 6B:
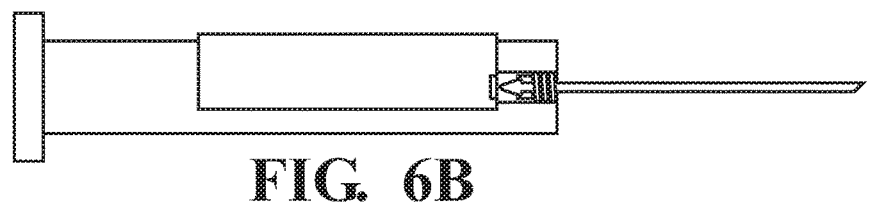
Figure 6C:
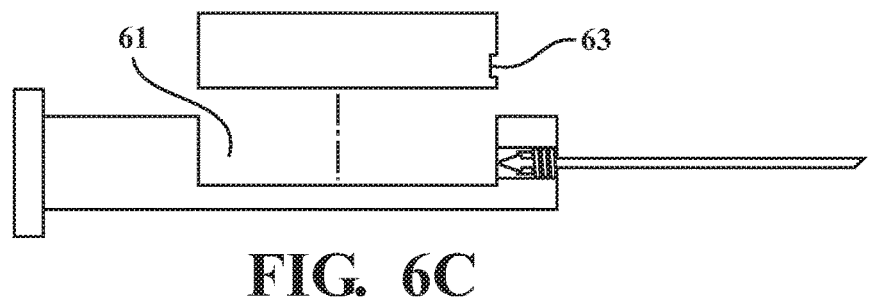

A number of options exist for possible cartridge removal, including but not limited to body compliance, mechanical release and by manually retracting the needle. FIGS. 6A-6C illustrate an example of a needle insertion simulator 60 with a detachable cartridge 66 showing a locking mechanism of the cartridge and the insertion and removal of the cartridge. The cartridge 66 may be inserted into a recess 61 of the syringe body 62 of the simulator 60. A spring 68 can be placed within the syringe body 62 and in front of the cartridge 66. When the spring is in a released position, the spring engages a recess 63 on the cartridge and locks the cartridge in place. When the spring is compressed to disengage the locking mechanism, as shown in FIGS. 6B-6C, the cartridge can be removed or inserted. The back end of the needle could be thin or could be thicker and wider to allow it to punch a bigger "hole" in the material.

Sensors

Figure 7:
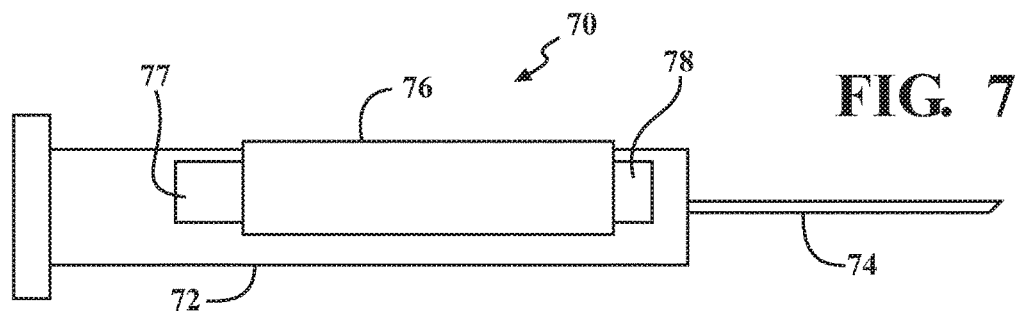
FIG. 7 is a cross-sectional view showing a haptic needle insertion simulator with a detachable cartridge with sensors in front of and behind the cartridge in accordance with an embodiment of the present invention.

Sensors may be located on a haptic simulation device for sensing position, orientation and movement of the device, needle positions inside the device, and type and position of the cartridge. The sensors can be installed behind or in front of a cartridge. FIG. 7 shows the cross-sectional view of a needle insertion simulator 70 having a syringe body 72, a cartridge 76 and a needle 74. The sensors may be placed at location 77 or 78, or other positions that provide the necessary performance. For example, a needle depth sensor may be placed in front of the cartridge 76 at the location 78. The sensors for sensing position, orientation and movement of the device or the sensors for sensing type and position of the cartridge may be placed behind the cartridge 76 at the location 77.

Sensing of Needle Movement and Orientation

Needle movement and orientation can be sensed with accelerometers, gyroscopes, magnetic trackers, imaging tracking, and/or Hall effect sensors.

Sensing Needle Position

The device can be configured to sense the needle position and relay this information to the computer program. The needle position may be sensed with linear encoders, rotary encoders, resistive sensors, hall effect sensors, optical sensors, infrared sensors, and/or ultrasonic sensors.

Sensing Cartridge Type And Position

The device may be configured to be capable of sensing the rotational position of the cartridge and the type of cartridge that is used and relaying this information to the computer program. The position of the cartridge may be sensed with hall effect sensors, optical sensors, ultrasonic sensors, resistive sensors, contact sensors, and/or pressure sensors. The locations of the punctures in the cartridge may be sensed with optical sensors, ultrasonic sensors, resistive sensors, contact sensors, and/or pressure sensors. The type of cartridge in the device may be sensed with bar code readers, magnetic sensors, contract sensors, and/or RFID sensors.

Figures 8A, 8B:
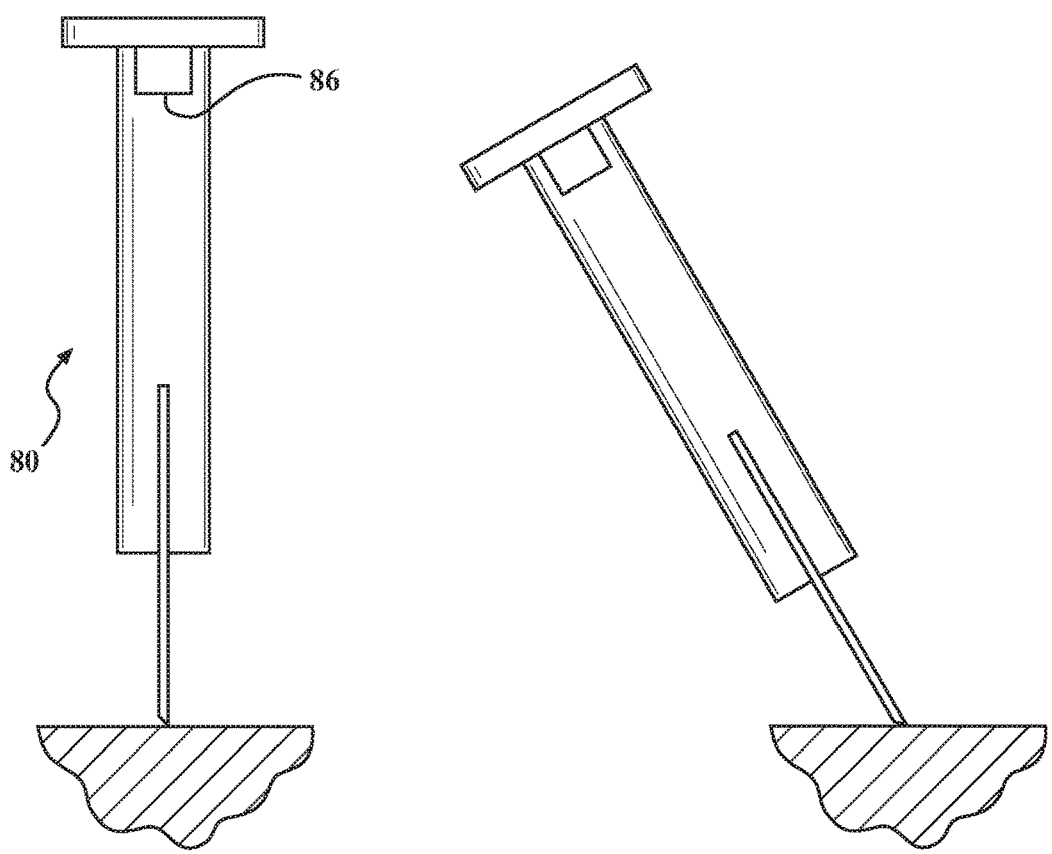
FIGS. 8A-8B are cross-sectional views showing a position and orientation sensor placed in a haptic needle insertion simulator for sensing position and orientation of the needle in accordance with another embodiment of the present invention.

FIGS. 8A-8B show another possible location for installing sensors. The needle syringe may 80 may contain sensors at the location 86 that will allow the needle tip position and needle orientation to be computed in space. These position sensors can be magnetic trackers, vision based sensors, compasses, hall effect sensors, gyroscope, and/or accelerometers. The position information from the needle syringe will be sent into a computer that will take this information and generate an appropriate ultrasound image Each of these possible sensors utilize an accurate references to accurately track orientation in time and space. For example, magnetic trackers utilize a magnetic reference to orient the device relative to static testing surface. Compass provides orientation using a reference north. Hall effect sensors use a fixed magnetic reference to provide orientation. Accelerometer can provide insertion angle using the fixed gravity acceleration as a reference. Gyroscope signal can provide accurate rotational speed information which can be used to determine rotational position after movement. The sensors' information may be coupled with one or more of the above sensors to enhance the real time position information.

In an example, the system 80 may have a low cost acceleration sensor 86 in the back of the syringe. This accelerometer will wirelessly communicate to a computer where custom software may:

1. Provide the user with immediate quantitative feedback about the steadiness and angle of their insertion and give the user an overall grade. The feedback will be directed to guide future improvement.
2. Provide the user with historical record of performance so that they can see their improvement.
3. Provide the user video tutorials of general strategies to improve performance.
4. Provide a 3$^{rd}$ party with the performance assessment information from the user. For example, the device may allow the instructor to evaluate a user's performance to verify completion of activity and competency level achieved to create effective learning feedback.

Figure 9:
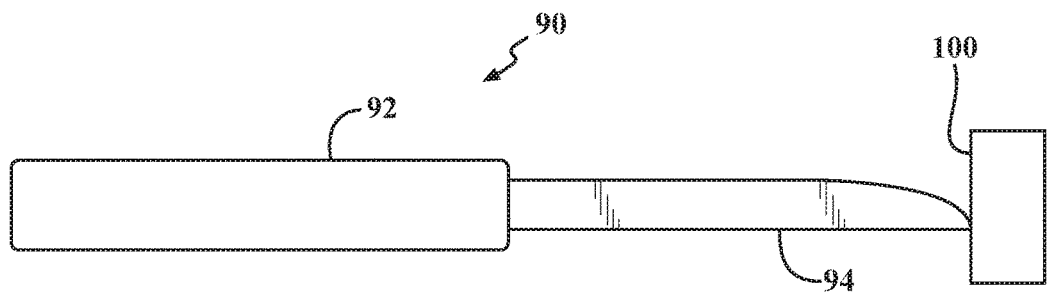
FIG. 9 is a cross-sectional view showing a haptic cutting tool in accordance with an embodiment of the present invention.

FIG. 9 provides a different embodiment of a haptic insertion simulator. In this embodiment, the medical instrument is a cutting tool 90 including a tool body 92 and a knife 94. The knife 94 can retract into the tool body when pushed against a surface 100.

Any of the concepts and embodiments discussed herein may be put into a cartridge version that could be taken off and exchanged for another. Similarly, any of the concepts or embodiments may instead be built into the device as permeant fixtures.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

The invention claimed is:

1. A haptic medical instrument insertion simulator, comprising:
    an instrument body;
    a retractable needle, blade or probe at one end of the instrument body, the retractable needle, blade or probe being operable to retract into the instrument body when pushed; and
    a cartridge disposed in the instrument body such that the retractable needle, blade or probe at least partially penetrates the cartridge when the retractable needle, blade or probe retracts into the instrument body,
    wherein the cartridge is configured such that the at least partial penetration creates a haptic force resistance felt by the user advancing the simulator, and
    wherein the instrument body is configured to provide a force profile simulating the haptic force resistance felt by a user advancing the simulator when the needle, blade or probe is being retracted into the instrument body.

2. The haptic medical instrument insertion simulator according to claim 1, wherein the cartridge is rotatable for repeated use.

3. The haptic medical instrument insertion simulator according to claim 1, wherein the cartridge is detachable from the instrument body.

4. The haptic medical instrument insertion simulator according to claim 1, further comprising a locking mechanism for locking the cartridge in a use position in the instrument body.

5. The haptic medical instrument insertion simulator according to claim 4, wherein the locking mechanism comprises one of:
    compliance of the cartridge with the instrument body;
    a mechanical release; and
    a locking mechanism operable to unlock by removing the needle.

6. The haptic medical instrument insertion simulator according to claim 1, further comprising a sensor for sensing a position and orientation of the needle, blade or probe.

7. The haptic medical instrument insertion simulator according to claim 1, further comprising a sensor for sensing movement and orientation of the needle, blade or probe.

8. The haptic medical instrument insertion simulator according to claim 1, further comprising a sensor for sensing cartridge type and position.

9. The haptic medical instrument insertion simulator according to claim 1, further comprising a sensor for sensing locations of punctures in the cartridge.

10. The haptic medical instrument insertion simulator according to claim 1, wherein the medical instrument is a needle and the instrument body is a syringe body.

11. A haptic medical instrument insertion simulator, comprising:
    an instrument body;
    a retractable needle, blade or probe at one end of the instrument body, the retractable needle, blade or probe being operable to retract into the instrument body when pushed; and
    an internal variable dampener for generating a haptic force resistance, the internal variable dampener being a cavity within the syringe body, the cavity having a variable profile and being filled with a fluid;
    wherein the instrument body is configured to provide a force profile simulating the haptic force resistance felt by a user advancing the simulator when the needle, blade or probe is being retracted into the instrument body.

12. The haptic medical instrument insertion simulator according to claim 11, further comprising a sensor for sensing a position and orientation of the needle, blade or probe.

13. The haptic medical instrument insertion simulator according to claim 11, further comprising a sensor for sensing movement and orientation of the needle, blade or probe.

14. The haptic medical instrument insertion simulator according to claim 11, wherein the medical instrument is a needle and the instrument body is a syringe body.

* * * * *